US007332126B2

(12) United States Patent
Tooke et al.

(10) Patent No.: US 7,332,126 B2
(45) Date of Patent: Feb. 19, 2008

(54) INTEGRATED MICROFLUIDIC DISC

(75) Inventors: Nigel Eric Tooke, Knivsta (SE); Per X. Andersson, Stockholm (SE)

(73) Assignee: GYROS Patent AB, Uppsala (SE)

( * ) Notice: Subject to any disclaimer, the term of this patent is extended or adjusted under 35 U.S.C. 154(b) by 374 days.

(21) Appl. No.: 11/034,539

(22) Filed: Jan. 13, 2005

(65) Prior Publication Data

US 2005/0202471 A1 Sep. 15, 2005

Related U.S. Application Data

(63) Continuation of application No. 10/168,942, filed as application No. PCT/EP00/13014 on Dec. 20, 2000, now Pat. No. 6,884,395.

(30) Foreign Application Priority Data

Dec. 23, 1999 (WO) ...................... PCT/EP99/10347
May 12, 2000 (GB) ................................ 0011425.6

(51) Int. Cl.
*B01D 21/26* (2006.01)
*B01D 61/00* (2006.01)
*C12Q 1/68* (2006.01)

(52) U.S. Cl. .......................... 422/64; 422/72; 422/101; 436/45; 436/63; 436/177; 435/91.2; 435/814; 210/651; 210/175; 210/198.2; 210/295; 210/304; 210/321.6; 210/380.1

(58) Field of Classification Search ................ 210/651, 210/175, 198.2, 295, 304, 321.6, 380.1; 422/72, 422/101, 64; 435/6, 91.2, 814; 436/63, 436/177, 45
See application file for complete search history.

(56) References Cited

U.S. PATENT DOCUMENTS

| | | | |
|---|---|---|---|
| 5,234,809 | A | 8/1993 | Boom et al. |
| 5,591,643 | A | 1/1997 | Schembri |
| 5,591,841 | A | 1/1997 | Ji et al. |
| 5,606,046 | A | 2/1997 | Woodard et al. |
| 5,610,074 | A | 3/1997 | Beritashvili et al. |

(Continued)

FOREIGN PATENT DOCUMENTS

WO WO 97/21090 6/1997

(Continued)

OTHER PUBLICATIONS

Christel et al., Rapid, Automated Nucleic Acid Probe Assays Using Silicon Microstructures for Nucleic Acid Concentration; Transactions of the ASME, vol. 121, Feb. 1999, 22-27.

(Continued)

*Primary Examiner*—David A Reifsnyder
(74) *Attorney, Agent, or Firm*—Fulbright & Jaworski LLP

(57) ABSTRACT

Disclosed is a method for performing the steps of nucleic acid template purification, thermocycling reaction and purification of the products of the thermocycling reaction characterized in that the steps take place sequentially in a microfluidic disc. Also disclosed is a microstructure for fluids comprising at least one inlet opening connected to a first chamber incorporating a means for purifying template nucleic acid which, in turn, is connected to a second chamber incorporating a means for a thermocycling reaction which, in turn, is connected to a third chamber incorporating a means for purifying products of the thermocycling reaction, and a microfluidic disc comprising a plurality of such microstructures.

6 Claims, 4 Drawing Sheets

U.S. PATENT DOCUMENTS

| | | | |
|---|---|---|---|
| 5,863,708 A | 1/1999 | Zanzucchi et al. | |
| 5,882,496 A | 3/1999 | Northrup et al. | |
| 6,013,513 A | 1/2000 | Reber et al. | |
| 6,117,630 A | 9/2000 | Reber et al. | |
| 6,319,469 B1 * | 11/2001 | Mian et al. | 422/72 |

FOREIGN PATENT DOCUMENTS

| | | |
|---|---|---|
| WO | WO 97/47767 | 12/1997 |
| WO | WO 99/12016 | 3/1999 |
| WO | WO 99/64848 | 12/1999 |
| WO | WO 00/37163 | 6/2000 |
| WO | WO 00/40750 | 7/2000 |

OTHER PUBLICATIONS

Shi, et al.; Radial Capillary Array Electrophoresis Microplate and Scanner for High-Performance Nucleic Acid Analysis; Anal Chem. 71, 1999, 5354-5361.

Zhang, et al.; Multiplexed Automated DNA Sequencing Directly from Single Bacterial Colonies; Anal.Chem, 71, 1999; 5018-5025.

Duffy et al, "Microfabricated Centrifugal Microfluidic Systems: Characterization and multiple Enzymatic Assays," Anal. Chem, vol. 71, 1999, pp. 4669-4678.

* cited by examiner centre of CD
Centrifugal force
outer edge of CD

INTEGRATED MICROFLUIDIC DISC

CROSS-REFERENCE TO RELATED APPLICATIONS

This application is a continuation of U.S. application Ser. No. 10/168,942 filed Sept. 25, 2002 now U.S. Pat. No. 6,884,395 which is the U.S. National Stage of International Application PCT/EP00/13014 filed Dec. 20, 2000 which claims priority to International Application PCT/EP99/10347 filed Dec. 23, 1999 and Great Britain Application No 0011425 filed May 12, 2000.

TECHNICAL FIELD

The present invention relates to a microfabricated apparatus comprising a rotatable disc, and particularly a microfluidic disc comprising microstructures for fluids, in which steps required for nucleic acid sequencing can be performed in an integrated and sequential manner.

BACKGROUND OF THE INVENTION

The process of sequencing has reached an industrial scale through the application of automation, particularly in the form of robots and handling of small volumes of liquid in multiplexed formats. The process typically involves fragmentation of a genome, insertion of fragments of interest into a cloning vector, isolation of individual clones, purification of the vector containing the inserted fragment and using that inserted fragment as a template in a sequencing reaction. The sequence data obtained is then aligned using software to obtain contiguous sequence from the numerous fragments. This process is described in more detail below.

Different cloning vectors can be used to clone fragments, depending on the size of the fragment. The purpose of cloning is to ensure replication of the insert to give large numbers of copies through a biological system (bacterium or virus). Large fragments are often cloned into BACs (Bacterial Artificial Chromosomes) or cosmids. Smaller fragments are commonly cloned either in bacterial plasmids such as pUC18 or in the phage M13.

A typical process for de novo sequencing of a genome using fragments cloned into a plasmid involves a number of possible steps performed sequentially. Examples of these steps are broadly described as follows:

1. Preparation of Bacterial Cultures

Fragments of the genome in question are created and inserted into plasmids (for example pUC18) that are maintained in a strain of the bacterium *Escherichia coli*. This process is termed transformation.

The transformed bacteria are spread out on an agar plate containing growth medium and an antibiotic to select for those bacteria that contain the plasmid (which bears a gene that confers antibiotic resistance to the host bacterium). The agar plate may also include an indicator that specifically shows the presence of bacteria containing plasmids that contain the insert—i.e. not just a clone containing an 'empty' or insert-free plasmid. The bacterial culture is diluted prior to being spread out to such an extent that individual bacterial cells, and hence their daughter colonies, are likely to be well separated from each other on the plate. This ensures that individual colonies are picked which in turn contain clones of only one sequence.

The plates are incubated overnight at 37° C. Individual bacterial cells give rise to colonies of cells that should not overlap on the plate.

Colonies are picked up either manually or by robot and may be used directly to prepare plasmids or, more commonly, to seed an over night liquid culture (typically 1-2 ml) to obtain larger amounts of bacteria and thus large numbers of copies of the insert.

2. Isolation of Plasmid Containing the Insert

The quality of the template nucleic acid is a key factor for success in a sequencing reaction. The template may be a plasmid or a polymerase chain reaction (PCR) product prepared from a plasmid. While there are reports of direct sequencing of bacterial extracts (see, for example, Frothingliam, R., R. L. Allen, et al. (1991). "Rapid 16S ribosomal DNA sequencing from a single colony without DNA extraction or purification." Biotechniques 11(1):40-4.; Chen, Q., C. Neville, et al. (1996)), most major sequencing facilities take great care to isolate pure plasmid in order to ensure sequencing success.

Many methods for plasmid isolation/purification have been developed. One common method is to (i) lyse bacterial cells using NaOH, (ii) precipitate protein and chromosomal DNA, (iii) isolate the plasmid in solution on glass matrix (or other purification column which selectively retains the nucleic acid to be isolated by adsorption or absorption) in the presence of a chaotrope such as guanidinium isothiocyanate (see for example U.S. Pat. No. 5,234,809) or sodium iodide, (iv) washing with an ethanolic solution to remove salts and other residual contaminants, and finally (v) elute the plasmid from the matrix with a low ionic strength buffer or water. The process also includes exposure to RNase to degrade RNA.

This method is the basis for a number of commercially available kits such as GFX Micro Plasmid Prep Kit (Amersham Pharmacia Biotech). These kits typically include a series of solutions, Solutions I, II and III wherein Solution I comprises approximately 100 mM Tris-HCl, pH 7.5, 10 mM EDTA, 400 μg/mL RNase I, Solution II comprises approximately 100 mM NaOH, 1% w/v SDS and Solution III comprises a buffered solution containing acetate and a chaotrope.

Modifications to the surface of the glass in the glass matrix are described, for example, in U.S. Pat. No. 5,606,046. Alternative methods include isolation by reversible, non-specific binding to magnetic beads in the presence of PEG and salt described, for example, in Hawkins, T. L., T. O'Connor-Morin, et al. (1994). "DNA purification and isolation using a solid-phase." Nucleic Acids Res 22(21): 4543-4, or by triplex-mediated affinity capture (U.S. Pat. No. 5,591,841). Suitable purification materials include gels, resins, membranes, glass or any other surface which selectively retains nucleic acids.

Plasmid quality can then be assessed using agarose gel electrophoresis and the quantity can be determined spectrophotometrically, both techniques being familiar to those skilled in the art. It is advantageous to obtain plasmid in water or dilute buffer that is compatible with the subsequent step (i.e. PCR or a direct sequencing reaction such as cycle sequencing).

If plasmid yield (or possible quality) is insufficient for direct sequencing then a specific region of the plasmid covering the insert and flanking sequence can be amplified by a conventional polymerase chain reaction (PCR) to give a sequencing template. This PCR product must be 'cleaned-up' before being used as template for sequencing. Clean up includes removal of unincorporated nucleotides and primers that would otherwise disturb the cycle sequencing reaction. One method involves exposure to exonuclease III and shrimp alkaline phosphatase, killing these enzymes by heat denaturation and using the reaction directly in cycle sequencing.

3. Cycle Sequencing

A cycle sequencing reaction involves mixing template nucleic acid with sequencing primers, a thermostable DNA polymerase enzyme and a mixture of the four deoxynucleotides (dATP, dCTP, dGTP and dTTP) including a small proportion of one base in a dideoxy (chain terminating) form, followed by cycles of heating and cooling (i.e. thermocycling). The reaction is run either in four different tubes—each containing having small amounts of each of the dideoxynucleotides, together with a fluorescently-labelled primer—or in one tube through the use of dideoxynucleotides with different fluorescent labels and unlabelled primer. The result is a fluorescently-labelled ladder of nucleic acid chains complementing the sequence of the template strand. Cycle sequencing reactions are commonly run in a scale of 10-20 μl in a microtitre plate (96-well or 384-well) in a thermocycler.

4. Clean Up

Where labelled nucleotide terminators are used, the reaction mixture should be 'cleaned up' afterwards in order to remove unincorporated fluorescent nucleotides. These would otherwise appear in the electrophoretic separation of the sequencing ladder and reduce the quality of the results.

In the case when capillary electrophoresis machines are used, it is also necessary to remove salts from the sequencing ladders in order to facilitate electrokinetic injection. This clean up is generally performed either by precipitation by addition of ethanol and salt, or by gel filtration. In the case of primer-labelled reactions, desalting is necessary only if capillary electrophoresis is to be used.

5. Analysis of Sequencing Reaction

The stopped sequencing reaction is then separated in a denaturing gel which may either be a slab-gel (as for example used in the ABI PRISM 377 or ALFexpress) or in capillary columns (as for example MegaBACE (Amersham Pharmacia Biotech) or PE ABI 3700 (PE Biosystems)) for subsequent analysis.

More recently, automation of these steps has been described with an emphasis on microfabrication i.e. performing these steps in as small volumes as possible.

The majority of automation efforts have aimed at the use of robots to carry out the steps normally done manually using pipettors and microtitre plates (96-well and 384-well). The individual steps are done in separate plates and liquid transfers between plates and formats are done by pipetting robots. More recently, attempts have been made to integrate various steps in one device, albeit comprised of a number of robots. One example is the Sequatron developed by Trevor Hawkins (Whitehead Institute). This consists of robots to purify M13 and carry out sequencing reactions in preparation for separation in ultra thin slab gels or capillaries. The technology is based on solid-phase isolation of DNA (see, for example, Hawkins, T. L., T. O'Connor-Morin, et al. (1994). "DNA purification and isolation using a solid-phase." Nucleic Acids Res 22(21): 4543-4) and makes possible throughputs in excess of 25,000 samples per 24 hours. In addition, a group at Washington University has developed robots for picking M13 plaques and template preparation again based on large robots and multititre plates.

Methods for isolation of DNA in the presence of chaotropes on micromachined silicon structures have been published (Christel, L. A., K. Petersen, et al. (1999). "Rapid, automated nucleic acid probe assays using silicon microstructures for nucleic acid concentration." J Biomech Eng 121(1):22-7). U.S. Pat. No. 5,882,496, describes the fabrication and use of porous silicon structures to increase surface area of heated reaction chambers, electrophoresis devices, and thermopneumatic sensor-actuators, chemical preconcentrates, and filtering or control flow devices. In particular, such high surface area or specific pore size porous silicon structures will be useful in significantly augmenting the adsorption, vaporization, desorption, condensation and flow of liquids and gasses in applications that use such processes on a miniature scale.

Methods for direct sequencing of plasmids from single bacterial colonies in fused-silica capillaries have been developed (Zhang, Y., H. Tan, et al. (1999). "Multiplexed automated DNA sequencing directly from single bacterial colonies." Analytical Chemistry 71(22): 5018-25). Alternative methods involve separation in glass chips including detection methods based on laser-excited confocal microscopy (see, for example, Kheterpal, I. and R. A. Mathies (1999). "Capillary array electrophoresis DNA sequencing." Analytical Chemistry 71(1): 31A-37A).

U.S. Pat. No. 5,610,074 describes a centrifugal rotor for the isolation, in a sequence of steps, of a substance from a mixture of substances dissolved, suspended or dispersed in a sample liquid. Multiple samples are processed simultaneously by means of a plurality of fractionation cells, each of which contains a series of interconnected, chambered and vented compartments in which individual steps of the fractionation and isolation procedure take place. In this centrifugal rotor, the specific compartment occupied by the sample liquid or one of its fractions at any stage of the process is governed by a combination both the speed and direction of rotation of the rotor and gravitational force. The interconnections, chambers and passages of each compartment are sized and angled to prevent predetermined amounts of sample and reagent liquids from overflowing the compartment. However, such a rotor is relatively bulky, requires relatively large volumes of solutions and is complicated to manufacture.

Micro-analysis systems that are based on microchannels formed in a rotatable, usually plastic, disc, are often called a "centrifugal rotor", "lab on a chip" or "CD devices". Such discs can be used to perform analysis and separation of small quantities of fluids. The principle of moving liquids through channels in a plastic disc for the purpose of carrying out enzymatic assays is described, for example, in Duffy, D. C., H. L. Gillis, et al. (1999). "Microfabricated centrifugal microfluidic systems characterization and multiple enzymatic assays." Analytical Chemistry 71(20): 4669-4678. One type of suitable plastic disc is those referred to as compact discs or CDs.

When such discs are rotated a centripetal force is directed towards the centre of the disc. Where fluid is in the disc, this centripetal force can be the result of several forces including surface tension, tensile forces and capillary force. Movement of fluids towards the outer diameter of the disc is achieved by overcoming the centripetal force, usually by increasing the rotational speed of the disc.

In order to reduce costs it is desirable that the discs should be not restricted to use with just one type of reagent or fluid but should be able to work with a variety of fluids. Furthermore it is often desirable during the preparation of samples that the disc permits the user to dispense accurate volumes of any desired combination of fluids or samples without modifying the disc. Due to the small widths of the microchannels, any air bubbles present between two samples of fluids in the microchannels can act as separation barriers or can block the microchannel and thereby can prevent a fluid from entering a microchannel that it is supposed to enter. In order to overcome this problem U.S. Pat. No. 5,591,643 teaches the use of a centrifugal rotor which has microchannels that have cross sectional areas which are sufficiently large that unwanted air can be vented out of the microchannel at the same time as the fluid enters the microchannel.

BRIEF SUMMARY OF THE INVENTION

The present invention relates to an apparatus for the integration of the steps of template isolation, cycle sequencing and cleanup into a CD device and to methods for using that apparatus. In particular the present invention relates to a single closed device capable of handling a large number of samples, thus greatly simplifying automation, reducing the reagent consumption and thus overall cost, and reducing the size of equipment required. To date, there have been no reports of an apparatus with a similar level of integration that allows isolation of a DNA template bacterial colony through to obtaining a cleaned-up sequencing reaction within a single enclosed structure.

Accordingly in a first aspect of the invention there is provided a method for performing a sequence of steps comprising.

a) the step of nucleic acid template purification;

b) the step of a thermocycling reaction; and c) the step of purification of the products of step b)

characterised in that the steps take place sequentially in a microfluidic disc.

Suitably, the nucleic acid template can be plasmid DNA although genomic eukaryotic or prokaryotic derived templates could also be used. Other nucleic acid templates can be purified from Bacterial Artificial Chromosomes (BACs) or phage M13 using appropriate extraction and purification protocols known to those skilled in the art.

In another embodiment, the thermocycling reaction can be performed directly on a simple bacterial extract without prior isolation of plasmid.

In a preferred embodiment of the first aspect, flow of fluid through the microfluidic disc can be effected by rotating the disc. The disc can be rotated (or spun) at variable speeds in the range of approximately 250 rpm (low speed) to 15,000 rpm (high speed). The actual speed that will be required to achieve correct flow of fluids through the disc at any particular stage of the method will depend on a number of factors including:

- the position of the structure on the microfluidic disc (i.e. the further the structure is from the centre of the disc, the lower the rpm required to achieve the same centrifugal force as in a structure nearer the centre of the disc);
- the physical dimensions of the structure through which the liquid must pass;
- the viscosity of the liquid; and
- the chemical and physical properties of the surfaces in the structure.

In a particularly preferred embodiment of the first aspect, the thermocycling reaction, step b), is a nucleic acid sequencing reaction or cycle sequencing reaction. Other preferred thermocycling reactions include polymerase chain reactions (PCR).

In another embodiment of the first aspect, the method further comprises.

d) the step of separation of the purified products obtained in step c); and, preferably, step d) is an electrophoretic separation of the products of the sequencing reaction. Preferably, the separation step d) also takes place in the same microfluidic disc as steps a)-c).

In a particularly preferred embodiments, step a) is performed by passing the nucleic acid template through a purification column in a microstructure comprised in a microfluidic disc, and step c) is performed by passing the products of step b) through a gel filtration column in a microstructure comprised in a microfluidic disc.

In one embodiment of the first aspect, there is provided a method for performing a nucleic acid sequencing reaction on a template nucleic acid, wherein the method comprises.

a) treating a culture of cells containing a template nucleic acid with a lysis reagent so as to lyse the cytoplasmic membranes;

b) introducing the lysate from step a) into microstructures for fluids on a microfluidic disc wherein each of said microstructures comprises a first chamber incorporating a means for purifying template nucleic acid, a second chamber incorporating a means for a thermocycling reaction and a third chamber incorporating a means for purifying products of the thermocycling reaction; and c) removing purified products for analysis.

In one embodiment, the purified products obtained after purification in the third chamber can be transferred to a capillary electrophoresis DNA sequencer (such as MegaBace™ (Amersham Pharmacia Biotech)) for analysis to obtain template sequence data. In another embodiment, the purified products could be analysed in a circular device directly linked to the 'sample preparation' microfluidic disc.

In another embodiment, the eluate from the first chamber might be initially directed into a volume definition structure to ensure accurate transfer of the correct volume of liquid into the second chamber incorporating a means for a thermocycling reaction.

In a second aspect of the invention there is provided a microstructure for fluids characterised in that it comprises.

a) at least one inlet opening; connected to b) a first chamber incorporating a means for purifying template nucleic acid; connected to c) a second chamber incorporating a means for a thermocycling reaction; connected to d) a third chamber incorporating a means for purifying products of the thermocycling reaction.

In a preferred embodiment of the second aspect, the microstructure for fluids further comprises:

e) a fourth chamber incorporating a means for applying an electric potential across a separation matrix connected to the third chamber.

In this embodiment of the invention, the electrophoretic separation of the sequencing ladder is performed in the same microfluidic disc or CD. Separation would be from the outer periphery of the circular device inwards to the centre where a single detector can detect the bands as they pass (described for example in Shi, Y., P. C. Simpson, et al. (1999). "Radial capillary array electrophoresis microplate and scanner for high-performance nucleic acid analysis." Analytical Chemistry 71(23): 5354-61). This would permit further reduction in the scale of sample preparation and a significant increase in the compactness and automation of the overall process.

Suitably, the chambers and channels comprising the microstructure may have depths in the range of approximately 10-500 microns.

In another embodiment of the second aspect, the microstructure for fluids further comprises a plurality of opening inlets and waste outlets arranged so as to enable introduction of sample and reagents and exit of waste products.

In a particularly preferred embodiment, the waste outlets can be connected to a vacuum pump for effective exit of waste.

In a third aspect of the invention, there is provided an apparatus for performing a thermocycling reaction on template nucleic acid which apparatus comprises a microfluidic disc, the disc comprising a plurality of radially dispersed microstructures for fluids according to the second aspect.

In one embodiment of the third aspect a number of microstructures are incorporated on a single microfluidic disc. In a preferred embodiment, the number of microstructures is between 1-1000, preferably, 80 to 100, arranged radially on a single disc. In a particularly preferred embodiment, 96 microstructures would be arranged on a single disc to make the disc apparatus compatible with 96 well assay formats.

Suitably the apparatus is formed of a 12 cm compact disc.

In another embodiment of the third aspect, the apparatus can further comprise a plurality of wells suitable for bacterial culture or initial nucleic acid template preparation on the same disc. This would have the advantage of removing the need for a format change between microtitre plate and microfluidic disc.

In a preferred embodiment, the opening inlets of the microstructures on the microfluidic disc are connect to a centralised distribution channel, such as a common annular channel, so as to allow centralised distribution of reagents into all the microstructures on a disc at the same time. Preferably the waste channels are connected by a common annular waste channel which, in one embodiment, can be orientated towards the outside periphery of the disc. Also preferred are a plurality of vents in the microstructures which allow for liquid flow through the integrated structure.

BRIEF DESCRIPTION OF THE DRAWINGS

The present invention will be illustrated by non-limiting examples of embodiments by means of the following figures, where.

DETAILED DESCRIPTION OF EMBODIMENTS ILLUSTRATING THE INVENTION

Figure 1A:
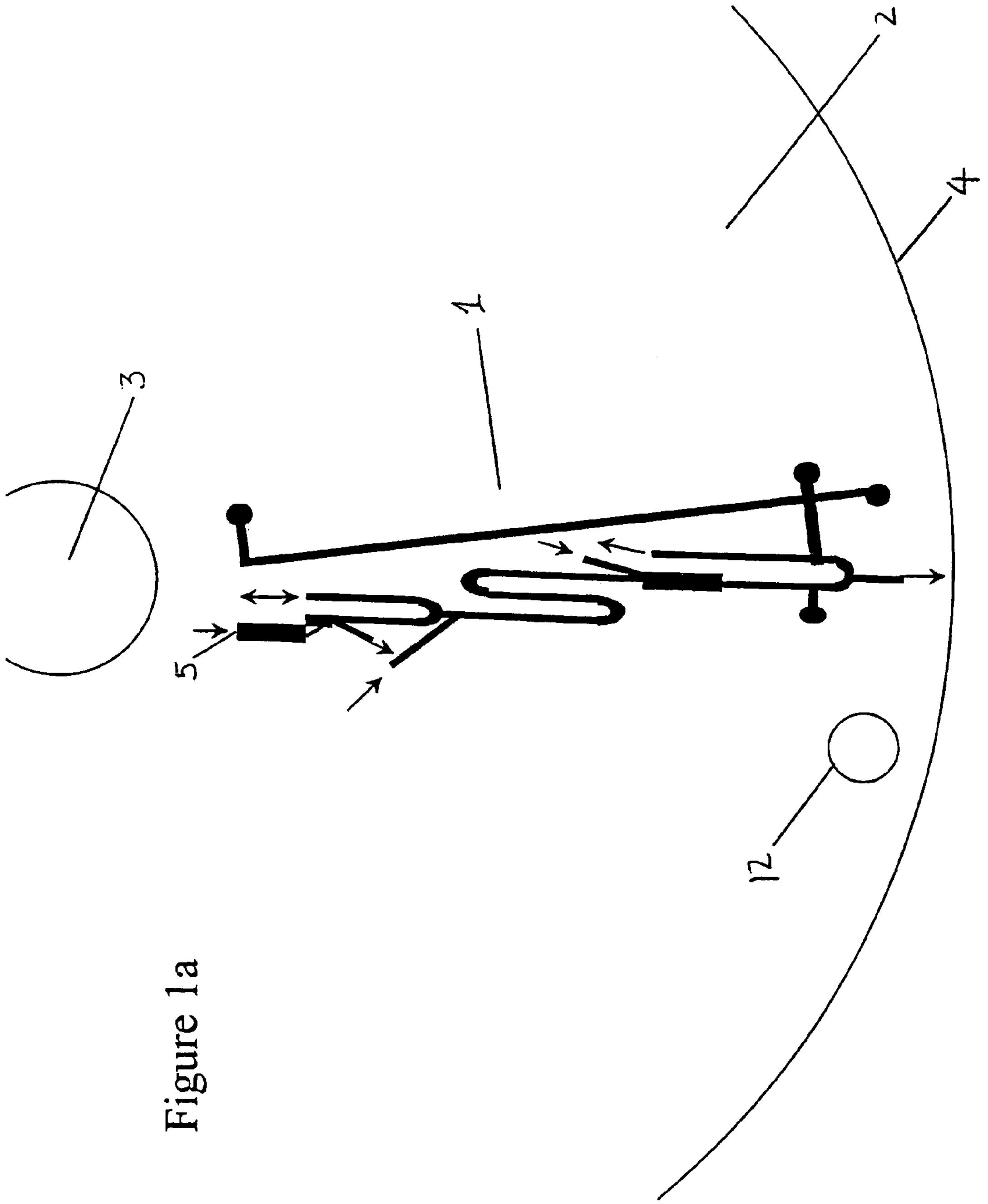
FIG. 1*a* shows a schematic diagram in plan of a microstructure for fluids in accordance with the present invention showing its orientation on a microfluidic disc (shown in part).

One example of a microstructure for fluids (1) in accordance with the present invention is shown in FIG. 1*a* arranged on a microfluidic disc (2) which is shown in part. The microstructure for fluids (1) is arranged radially on the disc with the inlet opening (5) being nearest to the central hole of the microfluidic disc (3). The outer edge of the microfluidic disc is shown (4). The microstructure for fluids is comprised of a series of connecting microchannels. The microfluidic disc (2) has a thickness which is much less than its diameter and is intended to be rotated around the central hole (3) so that centrifugal force causes fluid arranged in the microchannels in the disc to flow towards the outer edge or periphery (4) of the disc. Flow can be driven both by capillary action, pressure and centrifugal force, i.e. by spinning the disc. As described below, hydrophobic breaks can be used to control the flow.

Suitably the microfluidic disc is of a one- or two-piece moulded construction and is formed of an optionally transparent plastic or polymeric material by means of separate mouldings which are assembled together (e.g. by heating) to provide a closed structure with openings at defined positions to allow loading of the device with liquids and removal of liquid samples. Suitable plastics or polymeric materials may be selected to have hydrophobic properties. Preferred plastics or polymeric materials, preferably have low self fluorescence and are selected from polystyrene and polycarbonate. In the alternative, the surface of the microchannels may be additionally selectively modified by chemical or physical means to alter the surface properties so as to produce localised regions of hydrophobicity or hydrophilicity within the microchannels to confer a desired property. Preferred plastics are selected from polymers with a charged surface, suitably chemically or ion-plasma treated polystyrene, polycarbonate or other rigid transparent polymers.

The microchannels may be formed by micro-machining methods in which the micro-channels are micro-machined into the surface of the disc, and a cover plate, for example, a plastic film is adhered to the surface so as to enclose the channels.

Hydrophobic breaks can be introduced into the microchannel structures, for example by marking with an overhead pen (permanent ink) (Snowman pen, Japan).

The purpose of the hydrophobic breaks is to prevent capillary action from drawing the fluid into undesired directions. Hydrophobic breaks can be overcome by centrifugal force i.e. by spinning the disc at high speed.

In FIG. 1*a* the arrows show the direction of flow of fluids and/or air from inlet openings and waste outlets in the microstructure. These openings are described in more detail below.

FIG. 1*a* also shows a well (12) situated towards the outer edge (4) of the microfluidic disc. This well can be used for sample preparation prior to addition of the sample into inlet opening (5). For example, if the nucleic acid template to be used is derived from a bacterial colony, the bacterial colony may first be removed, for example, by pipetting robot, from the surface of a solid liquid medium by suspending it in approximately 10 μl of isotonic liquid. The suspension may then be placed in a well (12) on a microfluidic disc. The bacterial cells can then be pelleted by spinning the microfluidic disc and the supernatant may be discarded. The pellet may be resuspended in Solution I with subsequent spinning and resuspension in Solutions II and III consecutively. The precipitated genomic DNA and proteins are pelleted by spinning and the supernatant containing plasmid is processed further (see below).

Figures 1B, 1C, 1D:
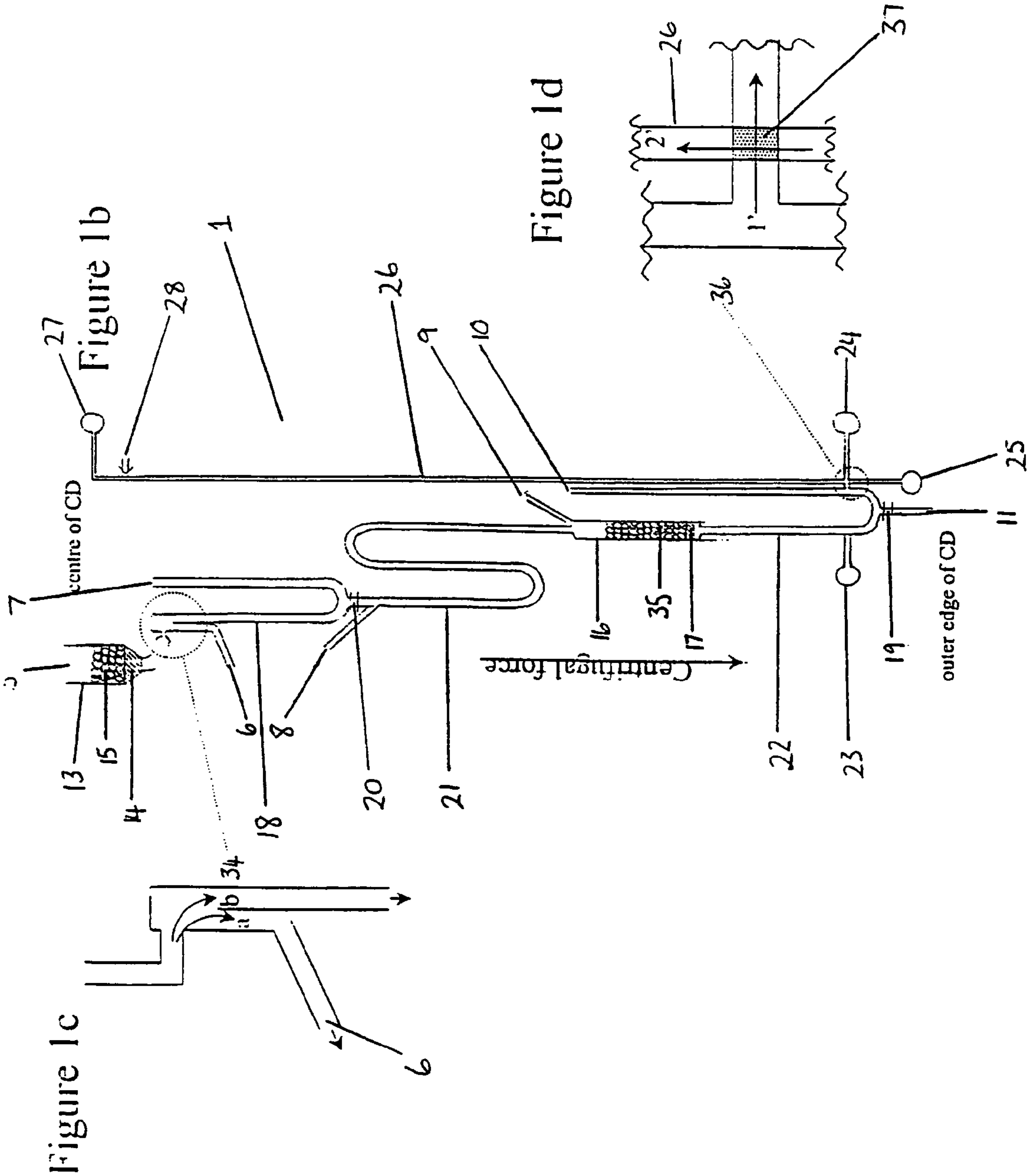
FIG. 1*b* shows a diagram in plan of one microstructure for fluids in accordance with the present invention.
FIG. 1*c* shows an enlarged view of the waste control structure (34) of the microchannel structure of FIG. 1*b*, wherein a shows the route of liquids when the microfluidic disc is spun at low speed, and b shows the route of liquids when the microfluidic disc is spun at high speed.
FIG. 1*d* shows an enlarged view of the region (36) between the sample preparation microchannel structure (i.e. parts (13)-(22)) and the electrophoresis structure (parts (23)-(28)) of the microstructure shown in FIG. 1*b;*

FIG. 1*b* shows a more detailed diagram of a microstructure for fluids (1).

The microstructure comprises inlet openings (5), (8) and (9) which may each be used as an application area for reagents and samples, waste outlets (6) and (11), a vent (10)

and an opening which can act as both inlet opening and vent (7). The vents open into open air via the top surface of the disc and prevent fluid in the microchannels from being sucked back into the structure.

Suitably, the inlet openings and waste outlets can be joined to an annular distribution channel.

Suitably, the waste outlets can be connected to a vacuum so that removal of waste can be facilitated.

The microstructure further comprises a series of chambers. The movement of liquids through the microchannels and chambers when the microfluidic disc is in use will now be described.

Prior to sample addition two purification columns are introduced into the microstructure as follows:

1. Naked Sephasil in liquid suspension is introduced into a first chamber (13) through inlet opening (5) and the microfluidic disc spun. The movement of the Sephasil is stopped by a change in depth from >20μ to <10μ (shown as shaded region (14)) to form a Sephasil column (15). Other suitable matrices should, preferably, be monodisperse spheres which are easy to pack and have a diameter in the range 15-50 μm.

FIG. 1*c* shows an enlarged view of a waste control structure (34) shown in the microchannel structure of FIG. 1*b* which allows removal of the liquid from the Sephasil suspension. Upon spinning the disc at low speed, the waste liquid from the Sephasil suspension will follow the wall of the nearest outlet (i.e. the direction indicated by arrow a) and exits the structure through a waste outlet (6).

2. Sephadex G-50 (DNA grade) in liquid suspension is introduced into chamber (16) through inlet opening (9). Upon spinning the microfluidic disc, the movement of the Sephadex G-50 out of chamber (16) is stopped by a change in depth from >20 m to <10 m (indicated by shaded region (17)) to form a Sephadex G50 bed, (35).

The liquid from the suspension is removed by applying sufficient centrifugal force (by spinning the microfluidic disc) such that it exits the microstructure through waste outlet (11), having passed a control region (19). Region (19) controls liquid flow by physical constriction of the channel and/or increased surface hydrophobicity so that liquid breaks through the resulting fluidic barrier only when a certain centrifugal forceis reached by spinning the microfluidic disc.

The microfluidic disc is now ready for sample addition.

Where the sample is bacterial plasmid nucleic acid, the supernatant from bacterial lysis is added to the first chamber (13) via inlet opening (5). By applying a centrifugal force, the sample is passed through the Sephasil column (15). Plasmid is captured on the Sephasil and washed with a wash solution introduced into chamber (13) again through inlet opening (5) and by spinning the microfluidic disc at low speed, the wash solution is caused to move through the Sephasil into the waste control structure (34) from which it exits the microstructure through waste outlet (6).

Plasmid is eluted from the Sephasil column by adding water to chamber (13) through inlet opening (5) and applying a higher centripetal force such that the eluate passes into the outer channel of the waste control structure (34) (i.e. the direction indicated by arrow b) and into the second chamber (18), a U-bend structure. Liquid flow is controlled, where necessary, by dimensional changes and/or changes in surface hydrophobicity in control region (20): region (20) may control liquid flow by physical constriction of the channel and/or increased surface hydrophobicity so that liquid breaks through the resulting fluidic barrier only when a certain centrifugal force is reached by spinning the microfluidic disc.

The liquid in chamber (18) is moved into a third chamber (21), a double-U structure, by centrifugal force. Simultaneously, reagents for performing cycle sequencing are introduced through inlet opening (8). Thus plasmid eluate and sequencing reagents are mixed in chamber (21).

A cycle sequencing reaction is performed by cycling the temperature of chamber (21) between approximately 60° C. and 95° C. whilst rotating the microfluidic disc in order to reduce evaporation in the chamber and also to reduce the risk of breaking the liquid column by bubble formation. Suitably, the reaction volume for the cycle sequencing reaction may be between 250-500 nl.

When cycling is complete a liquid plug is introduced into chamber (18) through inlet opening (7) and the liquid plug used to displace the liquid in chamber (21) and force it through the Sephadex bed in a fourth chamber (16) and further into a second U-bend structure, chamber (22). In this way salt and unincorporated dye terminators are retained in the Sephadex and thus removed from the sequencing reaction through the process of gel filtration. The purified reaction products (i.e. the ladder of sequencing products) are retained in chamber (22). Suitably, the reaction products will be in a volume of approximately less than 500 nanolitres.

A medium for electrophoresis, such as a high viscosity gel matrix, is introduced into channel (26), together with suitable buffers in the channels leading from chambers (23), (24), (25) and (27).

Referring to FIG. 1*d*, an electric potential is applied between chambers (23) and (24) such that the plug of purified reaction products passes in the direction indicated by arrow 1' from chamber (22) into the gel matrix in channel (26). A decrease in depth is indicated (37) which restricts movement of the high viscosity gel matrix and retains it in channel (26).

An electric potential is applied between chambers (25) and (27) such that the reaction products (sequence ladder) are moved through the gel matrix in channel (26) in the direction indicated by arrow 2' and, thus, separated. The products can be detected when passing point (28), thus generating information leading to the base sequence of the DNA in the plasmid.

Figure 1E:
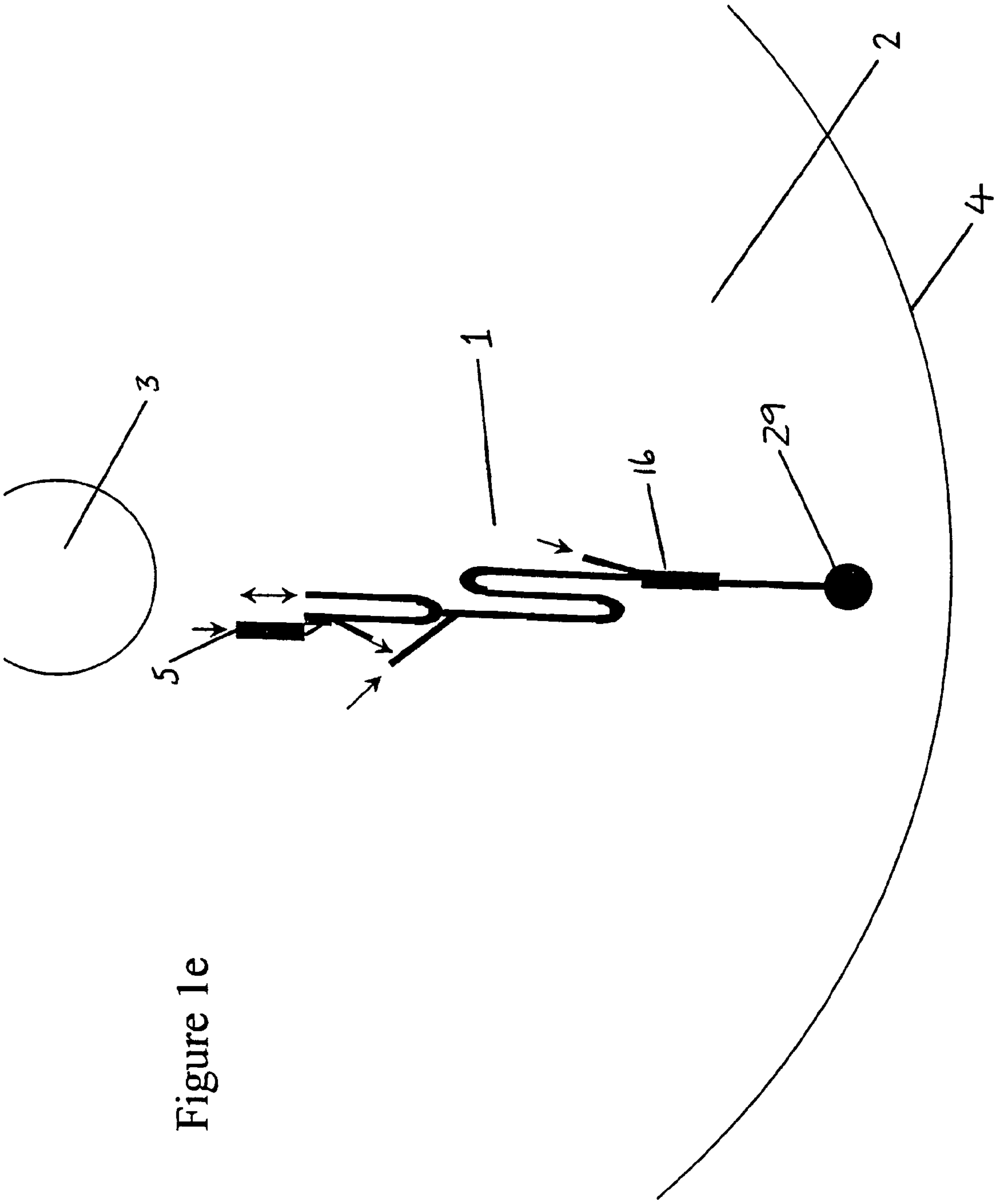
FIG. 1*e* shows an alternative embodiment of a microstructure for fluids in accordance with the invention arranged on a microfluidic disc (shown in part)

In the alternative embodiment of the microstructure in accordance with the invention depicted in FIG. 1*e*, the electrophoretic structure depicted in FIG. 1*b* as chambers (23)-(25), (27) and (28) and the channel (26) are absent. In this embodiment, the purified products of the thermocycling reaction (i.e. the eluate from chamber (16)) are retained a well (29) for transfer to a separate electrophoretic device. In this embodiment, the products will be obtained in an approximately submicrolitre volume which can be diluted by the addition of a liquid (e.g. formamide or water) for transfer into a separate structure for further analysis.

Figure 2:
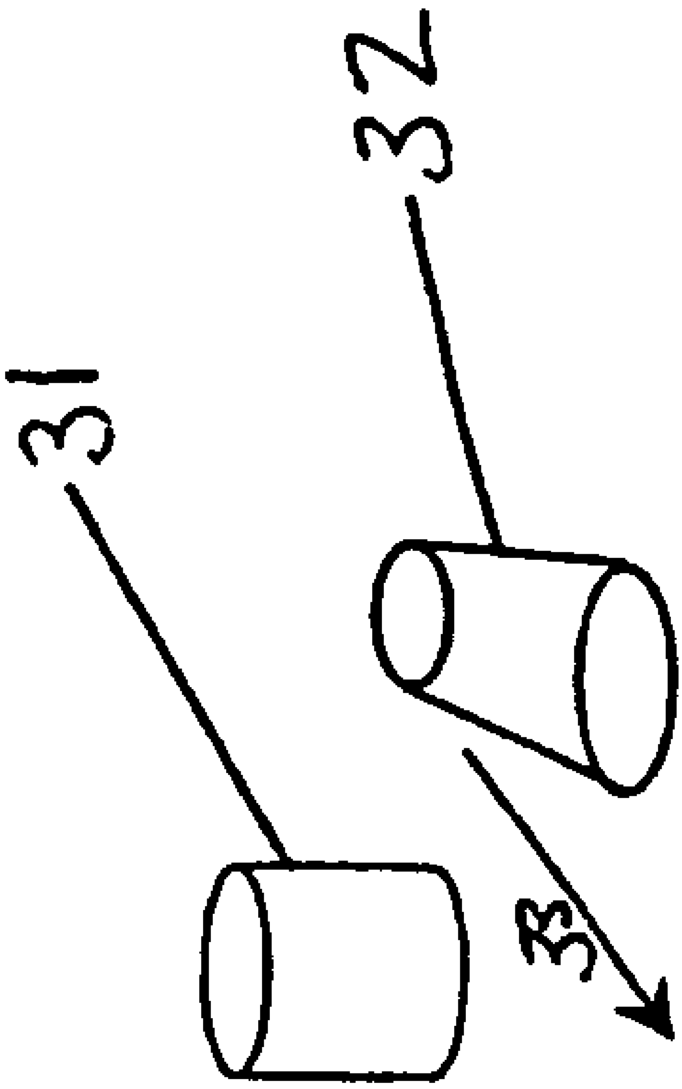
FIG. 2 shows two possible constructions for wells on a microfluidic disc in accordance with the present invention.

FIG. 2 shows a side view of two possible constructions of wells such as wells (12) and (29). One suitable well is cylindrical in shape (31). The other is frustroconical in shape (32); the shape of both the top and bottom of the well being substantially circular and the bottom circle having a larger diameter than the diameter of the top circle. The direction of the centrifugal force is indicated by the arrow (33).

The invention is further described with reference to the following non-limiting example.

EXAMPLE 1

1. Transformed bacteria are spread out on an agar plate containing LB medium+glucose with 100 mg/ml ampicillin and even indicator. The plate is incubated over night at 37° C.

2. Colonies derived from single bacterial cells (clones) are identified by eye (or using a robot). The colony is transferred to well in a microfluidic disc by resuspension in approximately 10 ml of an isotonic solution.

3. The bacterial cells are spun down by centrifugation and the supernatant is removed.

4. Three microlitres of Solution I (100 mM Tris-HCl, pH 7.5, 10 MM EDTA, 400 mg/ml RNase I) are added and the bacterial cells are resuspended by pipetting robot and incubated for 3 minutes (NOTE: all reagents for plasmid preparation taken from GFX Micro Plasmid Prep Kit, Amersham Pharmacia Biotech).

5. Three microlitres of Solution II (190 mM NaOH, 1% w/v SDS) are added with mixing by pipetting robot followed by incubation for 3 minutes.

6. Six microlitres of Solution III (buffered solution containing acetate and chaotrope) are added with mixing by pipetting robot.

7. The mixture is centrifuged and the supernatant is transferred to a structure for plasmid isolation.

8. The supernatant is passed through a bed of naked Sephasil beads (prepared in advance by addition of Sephasil to the microstructure and spinning the microfluidic disc at approximately 1000 rpm to remove the liquid) captured at the interface between deep and shallow sections in the structure. Plasmid is captured on the Sephasil column and, on spinning the microfluidic disc, unbound material passes out through a waste channel.

9. The column is washed with Wash Solution (Tris-EDTA buffer containing 80% ethanol) to remove contaminating proteins. Again, washings are redirected to waste by spinning the microfluidic disc at approximately 1000 rpm.

10. The plasmid is eluted by addition of 1-2 ml of water followed by spinning at higher speed. This eluate is directed into a thermocycling chamber where cycle sequencing is to be performed in a total volume of 250-500 nl.

11. In parallel to step 10, cycle sequencing reagents (enzyme, primer, buffer, nucleotides and fluorescent terminators) (obtained from DYEnamic ET dye terminator kit (MegaBACE™)) are introduced into the same thermocycling chamber.

12. Thermocycling is performed by alternating application of heat and cold to the chamber to provide a cycling between 95° C. and approximately 60° C. for 25-35 cycles.

13. The reaction mixture is ejected from the thermocycling chamber by centrifugal force and passes through a gel-filtration chamber. The gel-filtration chamber consists of monodisperse (sieved) Sephadex G-50 DNA grade beads captured at the interface between deep and shallow sections in the microstructure. Unincorporated terminators and also salt are retained. The remaining sequencing ladder continues into a final 'pickup' well, where necessary, more water is added to aid liquid handling and reduce evaporation.

14. The cleaned-up reaction is removed from the pick-up well by pipetting robot and placed in a microtitre plate and diluted to 5-10 ml for further processing by MegaBACE.

The invention claimed is:

1. An integrated microfluidic disc having at least one microstructure for fluids that is capable of performing template nucleic acid isolation, thermocycling reaction and purification of a thermocycling reaction product, wherein the microstructure comprises:

an inlet opening;

a first chamber having a means for isolating the template nucleic acid;

a second chamber having a means for performing a thermocycling reaction on said template nucleic acid producing a thermocycling reaction product; and a third chamber having a means for purifying the thermocycling reaction product, wherein the inlet opening is connected to the first chamber that is connected to the second chamber that is connected to the third chamber.

2. The disc of claim 1 further comprising a fourth chamber having a means for separating the purified thermocycling reaction product, wherein the fourth chamber is connected to the third chamber.

3. The disc of claim 2 wherein the separation means comprises an electrophoretic separation.

4. The disc of claim 1 wherein the flow of fluid through the microfluidic disc is controlled by rotating the disc.

5. The disc of claim 1 wherein the microstructure is arranged radially on the microfluidic disc.

6. The disc of claim 1 further comprising a plurality of radially arranged microstructures on the microfluidic disc.

* * * * *